United States Patent [19]
Chou

[11] Patent Number: 5,401,838
[45] Date of Patent: * Mar. 28, 1995

[54] STEREOSELECTIVE FUSION GLYCOSYLATION PROCESS FOR PREPARING 2'-DEOXY-2',2'-DIFLUORONUCLEOSIDES AND 2'-DEOXY-2'-FLUORONUCLEOSIDES

[75] Inventor: Ta-Sen Chou, Indianapolis, Ind.

[73] Assignee: Eli Lilly and Company, Indianapolis, Ind.

[*] Notice: The portion of the term of this patent subsequent to Dec. 6, 2011 has been disclaimed.

[21] Appl. No.: 44,343

[22] Filed: Apr. 7, 1993

Related U.S. Application Data

[63] Continuation-in-part of Ser. No. 902,312, Jun. 22, 1992.

[51] Int. Cl.$^6$ .......................................... C07H 19/073
[52] U.S. Cl. ................... 536/28.1; 536/28.4; 536/28.5; 536/28.51; 536/28.52; 536/28.53; 536/28.54; 536/28.55
[58] Field of Search ............... 536/27.11, 27.12, 27.13, 536/27.21, 28.1, 28.5, 28.53, 28.54, 28.4, 28.52

[56] References Cited

U.S. PATENT DOCUMENTS

| | | |
|---|---|---|
| 3,282,921 | 11/1966 | Verheyden et al. ................ 260/211 |
| 4,145,531 | 3/1979 | Eckstein et al. ..................... 536/26 |
| 4,211,773 | 7/1980 | Lopez et al. ........................ 536/28.5 |
| 4,526,988 | 7/1985 | Hertel .................................. 536/28.5 |
| 4,625,020 | 11/1986 | Brundidge et al. .................. 536/18 |
| 4,751,221 | 6/1988 | Watanabe et al. ................... 514/46 |
| 4,965,374 | 10/1990 | Chou et al. .......................... 549/313 |

FOREIGN PATENT DOCUMENTS

| | | | |
|---|---|---|---|
| 145978 | 6/1985 | European Pat. Off. ..... | C07H 13/00 |
| 211354 | 2/1987 | European Pat. Off. ... | C07H 19/073 |
| 219829 | 4/1987 | European Pat. Off. ..... | C07H 19/16 |
| 399161 | 11/1989 | European Pat. Off. ....... | C07F 9/65 |
| 345751 | 12/1989 | European Pat. Off. ..... | A61K 31/70 |
| 428109 | 5/1991 | European Pat. Off. ..... | C07H 19/19 |
| 2125401 | 3/1984 | United Kingdom . | |

OTHER PUBLICATIONS

Chem. Abstracts, 56, 11692–93 (1962).
R. P. Hodge, et al., J. Org. Chem., 56, 1553–64 (1991).
Hubbard, et al., Nucleic Acids Res., 12(17), 6827–37 (1984).
Kazimierczuk, et al., Nucleic Acids Res., 12(2), 1179–92 (1984).
Vorbruggen, et al., J. Org. Chem., 41(12), 2084–86 (1976).
Griengl, et al., J. Med. Chem., 28(11), 1679–84 (1985).
Tann, et al., J. Org. Chem., 50, 3644–47 (1985).
Howell, et al., J. Org. Chem., 53, 85–88 (1988).
Shimadate, et al., Nippon Kagaku Zasshi, 82, 1268–70 (1961).
Shimdate, et al., Nippon Kagaku Zasshi, 81, 1440–41 (1960).
Hoffer, Chem. Ber., 93, 2777–81 (1960).

Primary Examiner—John W. Rollins
Assistant Examiner—James O. Wilson
Attorney, Agent, or Firm—Sidney Persley; Robert A. Conrad; David E. Boone

[57] ABSTRACT

A stereoselective fusion glycosylation process for prearing beta-anomer enriched 2'-deoxy-2',2'-difluoronucleotides and 2'-deoxy-2'-fluoronucleosides by reacting an alpha-anomer enriched 2-deoxy-2,2-difluorocarbohydrate or 2-deoxy-2-fluorcarbohydrate with at least a 3 molar equivalent of a nucleobase derivative at a temperature sufficient to melt the carbohydrate and nucleobase derivative.

18 Claims, No Drawings

STEREOSELECTIVE FUSION GLYCOSYLATION PROCESS FOR PREPARING 2'-DEOXY-2',2'-DIFLUORONUCLEOSIDES AND 2'-DEOXY-2'-FLUORONUCLEOSIDES

CROSS REFERENCE TO RELATED APPLICATION

This application is a continuation-in-part of Ser. No. 07/902,312, filed Jun. 22, 1992.

BACKGROUND OF THE INVENTION

Field of the Invention

The invention pertains to the field of pharmaceutical chemistry and provides a stereoselective fusion glycosylation process for preparing 2'-deoxy-2',2'-difluoronucleosides and 2'-deoxy-2'-fluoronucleosides.

State Of the Art

The continued interest in the synthesis of 2'-deoxynucleosides and their analogues is reflected in their successful use as therapeutic agents in viral and cancerous diseases. A critical step in the synthesis of 2'-deoxynucleosides is the condensation of the nucleobase and carbohydrate to form the N-glycosidic bond. When the carbohydrate possesses a 2-hydroxy substituent, the substituent provides a substantial degree of 1,2-anchiomeric assistance, which facilitates stereoselective glycosylation. However, processes for synthesizing of 2'-deoxynucleosides are typically non-stereoselective and form a mixture of alpha and beta nucleosides.

Another type of condensation is fusion glycosylation, which is carried out in the absence of a solvent and at reaction temperatures sufficient to convert the carbohydrate and nucleoside base reactants to a molten phase. The original fusion glycosylation process was used to prepare purine nucleosides and involved reacting a peracylated sugar with a fusible purine base under vacuum and in the presence of a catalyst, such as p-toluenesulfonic acid. However, the glycosylation was not effective in condensing pyrimidine nucleosides because of their high melting points. In addition, the yields would vary widely and a broad range of anomerically mixed nucleoside products were produced.

T. Shimadate, et al., in *Nippon Kagaku Zasshi*, 81, 1440–1444 (1960) and *Chem. Abstracts*, 56, 11692 (1962), described a fusion glycosylation process involving reacting a peracylated arabinofuranose and a purine base in the molten phase, under vacuum, in the presence of a p-toluenesulfonic acid catalyst. T. Shimadate, *Nippon Kagaku Zasshi*, 92, 1268–1270 (1961), described a similar fusion glycosylation process using an anhydrous zinc dichloride catalyst.

R. P. Hodge, et al., *J. Org. Chem.*, 56, 1553–1564 (1991), described the preparation of deoxythymidine, deoxycytidine, deoxyadenosine and deoxyguanosine nucleosides containing deuterium at the C-1' position of the carbohydrate 1-chloro-3,5-ditoluoylribofuranose. The glycosylation was based on the synthesis described in Hubbard, et al., *Nucleic Acids Res.*, 12, 6827 (1984). The preparation of 2'-deoxycytidine required converting a silylated uridine derivative to a silylated cytidine derivative by one of the three different methods. In each, substantial quantities of undesirable alpha-anomer nucleoside product formed. Also, isolating the small quantity of beta-anomer nucleoside obtained from the anomeric mixture proved to be difficult.

The synthesis of purine deoxynucleosides was carried out by the procedure described in Robbins, *Nucleic Acids Res.*, 12, 1179 (1984), and involved reacting a sodium salt of a halopurine with 1-chloro-3,5-ditoluoylribofuranose. The sodium salts of purine bases were found to be much better nucleophiles than silylated pyrimidine bases.

U.S. Pat. No. 4,526,988, Hertel, illustrated a fusion glycosylation process for preparing 2'-deoxy-2',2'-difluoronucleosides which involves reacting a 3,5-bis(t-butyldimethylsilyloxy)-1-methanesulfonyloxy-2-deoxy-2,2-difluororibofuranose with 5-methyl-2,4-bis(trimethylsilyloxy)-pyrimidine at 150° C.

Vorbruggen, et al., *J. Org. Chem.*, 41, 2084 (1976) provided an outstanding development in the field of glycosylation and showed how nucleosides may be obtained from the Friedel-Crafts catalyzed reaction of a peracylated carbohydrate and silylated heterocycles in a solvent such as, 1,2-dichloroethane and acetonitrile. But when this process was applied to the synthesis 2'-deoxynucleosides, a 1:1 alpha to beta-anomeric mixture of nucleoside products was produced. Recent reports, for example, Grienyl, et. al., *J. Med. Chem.*, 28, 1679 (1985), have indicated that condensation reactions carried out in chloroform show a preference for beta-anomer nucleosides in a 3:1 beta to alpha ratio.

Some deoxynucleosides have been prepared in high yield from deoxyhalogenose with Friedel-Crafts catalysts, notably, 1-chloro-2-deoxy-3,5-di-p-toluoyl-alpha-D-erythropentofuranose; see, M. Hofer, *Chem. Ber*, 93, 2777 (1960). However, halogenoses are less stable thermally than peracylated carbohydrates and produce a 1:1 alpha to beta-anomeric mixture of nucleoside products. Walker, et al., *Nucleic Acid Research*, 12, 6827 (1984), used halogenose in condensation reactions to study the factors controlling the anomeric ratio of nucleoside products and found that beta-anomer nucleosides were formed exclusively from alpha-halocarbohydrates via $S_N2$ displacement. The corresponding alpha-anomer nucleoside contamination was determined to result from the anomerization of alpha-halo carbohydrate to beta-halo carbohydrate before the $S_N2$ displacement reaction. Walker et al., found that by changing the solvent or catalyst higher yields of the desired beta-anomer nucleoside were produced.

R. P. Hodge et. al., *J. Org. Chem.*, 6., 1553 (1991), described preparing pyrimidine and purine nucleosides containing deuterium at the C-1' position by the method described by Walker, et al. 1'-Deuterium-2'-deoxycytidine was prepared by reacting a carbohydrate and silylated cytosine derivative but the reaction gave poor yields. However, the yield was significantly improved when silylated uridine derivatives were used.

The synthesis of 2'-deoxy-2'-fluoronucleosides advanced rapidly when a procedure for synthesizing 2-deoxy-2-fluoro-3,5-di-O-benzoyl-alpha-D-arabinosyl bromide was made available; see Tann, et. al., *J. Org. Chem.*, 50, 3644 (1985) and Howell, et. al., *J. Org, Chem.*, 53, 85 (1988). It was discovered that 2-deoxy-2-fluoro-3,5-di-O-benzoyl-alpha-D-arabinosyl bromide did not anomerize in dry acetonitrile over extended periods. Therefore, high yields of beta-nucleosides could be obtained from 2-deoxy-2-fluoro-3,5-di-O-benzoyl-alpha-O-arabinosyl bromide via $S_N2$ displacement. Also, stereoselectivity of the nucleoside products could be achieved if either carbon tetrachloride or chloroform solvents was employed.

The formation of the N-glycoside bond in 2'-deoxy-2',2'-difluoronucleoside synthesis is much more difficult than in instances where the carbohydrate is 1,2-anchiomericly assisted or contains 2-deoxy-2-fluoro groups. The traditional carbohydrate leaving groups, such as those used in the Vorbruggen condensation method, acetate, chloride and bromide, render the carbohydrate inactive. In order to overcome this problem, Hertel, U.S. Pat. No. 4,526,988, described a modified version of the Vorbruggen condensation method that relied on more reactive sulfonate leaving groups attached to the carbohydrate to affect its reactivity. For example, hydroxy protected carbohydrates, such as 2-deoxy-2,2-difluoro-D-ribofuranose, containing a methanesulfonate, toluenesulfonate, ethanesulfonate, isopropanesulfonate or 4-methoxybenzenesulfonate leaving group at the C-1 position, were reacted with a protected nucleobase at temperatures of 50° C. to 220° C., in the presence of a high boiling solvent, such as dimethylformamide, dimethylacetamide and hexamethylphosphoramide. Hertel teaches that when carrying out the glycosylation reaction at elevated pressures, any convenient inert solvent, such as ethers, halogenated alkanes, and aromatics, can be used since the elevated pressure eliminates the loss of low boiling inert solvents due to evaporation. However, at reaction temperatures from room temperature to 100° C., a catalyst such as trifluoromethanesulfonyloxysilane, is required. U.S. Pat. No. 4,965,374, Chou, et al. reports that Hertel's condensation method provides alpha-anomer stereoselectively and therefore forms a 4:1 alpha to beta anomeric ratio of nucleoside products and goes on to describe an improved procedure, based on the Vorbruggen condensation method, that employs a pivotal intermediate of 2-deoxy-2,2-difluoro-3,5-di-O-benzoyl-alpha-D-arabinosyl methanesulfonate. However, Chou's condensation method forms a 1:1 alpha to beta anomer mixture of nucleoside products.

Despite the preceding advances in nucleoside synthesis, there continues to be a need for a stereoselective fusion glycosylation process capable of efficiently producing beta-anomer enriched 2'-deoxy-2',2'-difluoronucleosides and 2'-deoxy-2'-fluoronucleosides in increased yields.

Accordingly, one object of the present invention is to provide a stereoselective fusion glycosylation process for preparing beta-anomer enriched 2'-deoxy-2',2'-difluoronucleosides and 2'-deoxy-2'-fluoronucleosides.

Another object of the present invention is to provide a stereoselective fusion glycosylation process for preparing beta-anomer enriched 2'-deoxy-2',2'-difluoronucleosides and 2'-deoxy-2'-fluoronucleosides without the use of a catalyst.

Another object of the present invention is to provide a stereoselective fusion glycosylation process for preparing beta-anomer enriched 2'-deoxy-2',2'-difluoronucleosides and 2'-deoxy-2'-fluoronucleosides in yields higher than those produced by conventional fusion glycosylation procedures.

Yet another object of the present invention is to provide a stereoselective fusion glycosylation process for preparing beta-anomer enriched 2'-deoxy-2',2'-difluoronucleosides that offers a means for isolating intermediates of the beta-anomer enriched nucleosides as a crude product or acid addition salt such as a hydrochloride salt.

Other objects and advantages of the present invention will become apparent from the following description of embodiments.

SUMMARY OF THE INVENTION

The invention is a stereoselective fusion glycosylation process for preparing a beta-anomer enriched nucleoside of the formula

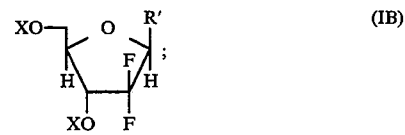

wherein each X is independently selected from hydroxy protecting groups and R' is a nucleobase moiety selected from the group consisting of

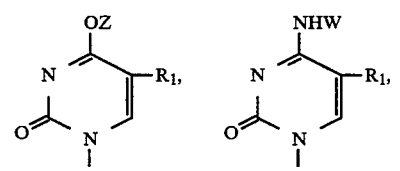

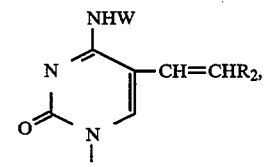

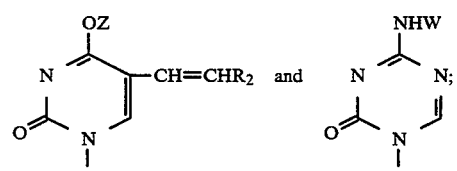

wherein $R_1$ is selected from the group consisting of hydrogen, alkyl and halo; $R_2$ is selected from the group consisting of hydrogen, alkyl and halo; Z is a hydroxy protecting group and W is an amino protecting group; comprising reacting an alpha-anomer enriched 2,2-difluorocarbohydrate of the formula

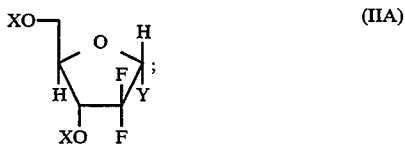

wherein Y selected from the group consisting of alkylsulfonyloxy, arylsulfonyloxy, substituted alkylsulfonyloxy and substituted arylsulfonyloxy and X is as defined above; with at least a molar equivalent of a nucleobase derivative, R", selected from the group consisting of

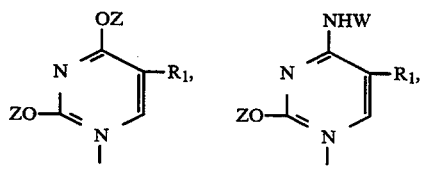

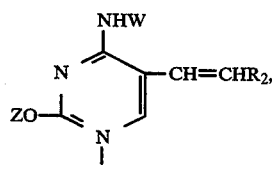

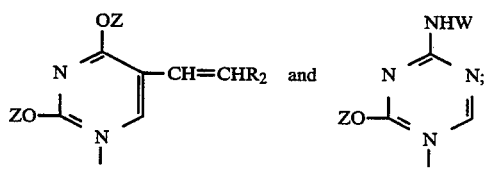

wherein $R_1$, $R_2$, Z and W are as defined above.

In another aspect, the invention is a stereoselective fusion glycosylation process for preparing a beta-anomer enriched nucleoside of the formula

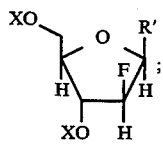 (IVB)

wherein X and R' are as defined above; comprising reacting an alpha-anomer enriched 2-monofluorocarbohydrate of the formula

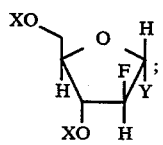 (VA)

wherein Y and X are as defined above; with at least a molar equivalent of a nucleobase derivative, R'', wherein R'' is as defined above.

This invention also provides a stereoselective fusion glycosylation process for preparing a beta-anomer enriched nucleoside of the formula

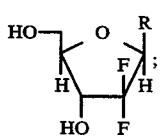 (VIB)

wherein R is a deblocked nucleobase selected from the group consisting of

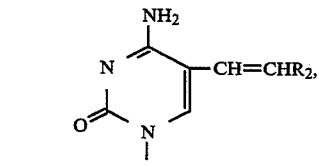

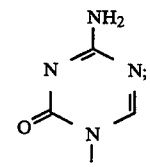

wherein $R_1$ is selected from the group consisting of hydrogen, alkyl and halo; $R_2$ is selected from the group consisting of hydrogen, alkyl and halo; comprising reacting a alpha-anomer enriched 2,2-difluorocarbohydrate of the formula

 (IIA)

wherein Y is selected from the group consisting of alkylsulfonyloxy, arylsulfonyloxy, substituted alkylsulfonyloxy and substituted arylsulfonyloxy and X is a hydroxy protecting group; with at least a molar equivalent of a nucleobase derivative, R''; wherein R'' is as defined above; and deblocking.

Also provided is a stereoselective fusion glycosylation process for preparing a beta-anomer enriched nucleoside of the formula

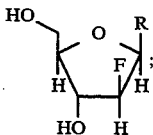 (VIIB)

wherein R is a deblocked nucleobase as defined above; comprising reacting a alpha-anomer enriched 2-fluorocarbohydrate of the formula

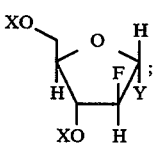 (VA)

wherein Y is selected from the group consisting of alkylsulfonyloxy, arylsulfonyloxy, substituted alkylsulfonyloxy and substituted arylsulfonyloxy and X is a hydroxy protecting group; with at least a molar equivalent of a nucleobase derivative R", wherein R" is as defined above; and deblocking.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or percent. The term "xylenes" alone or in combination refers to all isomers of xylene and mixtures thereof. The term "lactol" alone or in combination refers to a 2-deoxy-2,2-difluoro-D-ribofuranose or 2-deoxy-2-fluoro-D-ribofuranose. The term "carbohydrate" alone or in combination refers to an activated lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons such as chloroethyl, 1,2-dichloroethyl and the like. The term "alkoxy" alone or in combination refers to compounds of the general formula AO; wherein A is an alkyl. The term "aryl" alone or in combination refers to carbocyclic or heterocyclic groups such as phenyl, naphthyl, thienyl and substituted derivatives thereof. The term "aromatic" alone or in combination refers to benzene-like structures containing (4N+2) delocalized $\pi$ electrons. The terms "sulfonate" or sulfonyloxy" alone or in combination refer to compounds of the general formula $BSO_3$, wherein B is alkyl or aryl. The term "substituted" alone or in combination refers to a substitution by at least one or more of the groups selected from cyano, halo, carboalkoxy, toluoyl, nitro, alkoxy, alkyl, and dialkylamino. The phrase "anomer-enriched" alone or in combination refers to an anomeric mixture wherein the ratio of a specified alpha- or beta-anomer is greater than 1:1 and includes substantially pure anomer.

In accordance with the present fusion glycosylation process for preparing beta- and alpha-anomer enriched 2'-deoxy-2',2'-difluoronucleosides and 2'-deoxy-2'-fluoronucleosides of formulas I and IV, alpha- or beta-anomer enriched carbohydrates of formulas II and V are reacted with at least a molar equivalent of a nucleobase in the absence of a catalyst and a solvent, as represented in the following reaction schemes for making beta-anomer nucleosides:

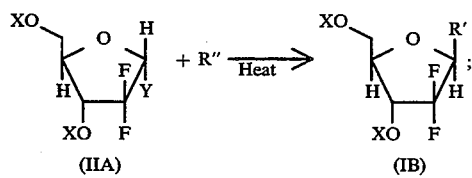

and

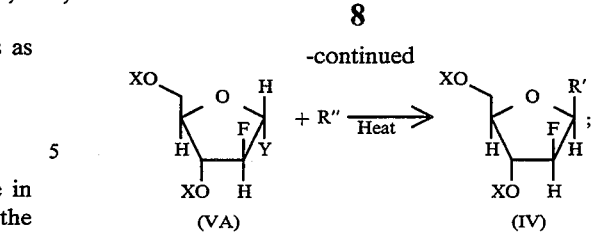

wherein Y, X, R" and R' are as defined above.

While not wishing to be bound by theory, it is believed that the glycosylation reaction proceeds primarily via $S_N2$ displacement. Therefore, the beta-anomer enriched nucleoside products are derived from alpha-anomer enriched carbohydrates. Conversely, the alpha-anomer enriched nucleoside products are derived from beta-anomer enriched carbohydrates.

The lactol starting materials suitable for use in the present fusion glycosylation process are commonly known in the art and can be readily synthesized by standard procedures commonly employed by those of ordinary skill in the art. For example, U.S. Pat. No. 4,526,988, teaches the synthesis of 2-deoxy-2,2-difluoro-D-ribofuranoses having the formula

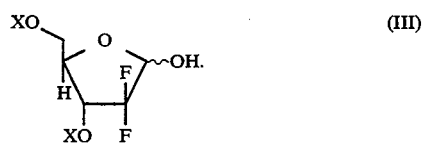

In addition, Reichman, et al., carbohydr. RES., 42,233 (1975) teaches the synthesis of 2-deoxy-2-fluoro-D-ribofuranoses of the formula

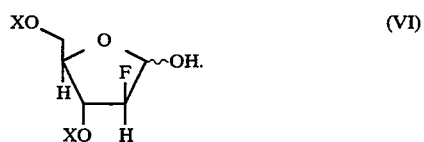

In a preferred embodiment, a 2-deoxy-2,2-difluoro-D-ribofuranose-3,5 dibenzoate of formula III is used to prepare the blocked nucleoside products under the present invention.

Glycosylation reactions typically require protecting the hydrogen atoms of the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is completed. Hydroxy protecting groups known in the art are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

In attaching each hydroxy protecting group (X) to the lactol, typical reaction conditions are employed and depend on the nature of the protecting group chosen. Suitable reaction conditions are discussed in U.S. Pat. No. 4,526,988 which is incorporated herein by reference.

To obtain an efficient reaction of the nucleobase derivative and carbohydrate, an appropriate leaving group is stereoselectively attached to the lactol of formulas III and VI which activates the lactol and generates the and alpha-anomer enriched carbohydrate of formulas II and V. The leaving group (Y) of the carbohydrate may be selected from the group consisting of alkylsulfonyloxy, arylsulfonyloxy, substituted alkylsulfonyloxy and substituted arylsulfonyloxy; provided that trifluoromethanesulfonyloxy, 1,1,1-trifluoroethanesulfonyloxy, octafluorobutanesulfonyloxy ($C_4F_8HSO_3$) and nanofluorobutanesulfonyloxy ($C_4F_9SO_3$) are not used; however, more preferred are methanesulfonyloxy, 2-chloroethanesulfonyloxy, toluenesulfonyloxy, p-nitrobenzenesulfonyloxy and p-bromobenzenesulfonyloxy; while most preferred is methanesulfonyloxy.

The alpha-anomer enriched carbohydrate of formula II may be prepared by one of two methods. The alpha-anomer enriched carbohydrate of formula V is prepared by the second of these methods. The first method, described in U.S. Pat. No. 5,256,798, teaches treating a beta-anomer ribofuranosyl sulfonate or anomeric mixture thereof with a source of a conjugate anion of a sulfonic acid at elevated temperatures in an inert solvent. The second method is described in pending U.S. patent application Ser. No. 07/902,301, Attorney Docket X-8623, and teaches reacting the lactol of formulas III and VI, with an amine base such as triethylamine, tributylamine, dibutylamine, diethylmethylamine, dimethylethylamine, benzylmethylamine, N-methylmorpholine, tripropylamine, dipropylethylamine, N,N-dimethylbenzylamine, diisopropylethylamine, diethylamine, 1,8-diazabicyclo[5.4.0]undec-7-ene and 1,5-diazabicyclo[4.3.0]non-5-ene. The amine base preferably has a pKa of from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below −78° C. Preferred solvents are selected from the group consisting of dichloromethane, 1,2-dichloroethane, dichlorofluoromethane, acetone, toluene, anisole, chlorobenzene, and mixtures thereof. The temperature of the solvent mixture is adjusted preferably in the range from about −40° C. to about −120° C. and more preferably below about −78° C. While not wishing to be bound by theory it is believed that the low temperature shifts the alpha to beta anomeric ratio of the lactol in favor of the alpha-anomer in a range from about 2:1 to about 4:1 alpha to beta. For example, a compound of formula III, where X is benzoyl, was added to dichloromethane and triethylamine at room temperature for 30 minutes. Next, the temperature of the solvent mixture was lowered. An $^{19}F$ NMR, taken at various temperatures, shows an increase in the alpha to beta ratio of the ionized lactol as the temperature was lowered:

| Temperature | Alpha/Beta Ratio |
|---|---|
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is then trapped in solution at the low temperature and higher alpha-anomer ratio by adding a sulfonating reagent which forms an alpha-anomer enriched carbohydrate. The sulfonating reagents are selected from the group consisting of substituted and unsubstituted alkyl- and aryl-sulfonyl halides and alkyl- and arylsulfonic acid anhydrides such as methanesulfonyl chloride, depending on the leaving group desired.

The alpha-anomer enriched carbohydrate may be isolated in substantially pure form; i.e. greater 95 percent purity; by the procedure described in U.S. Pat. No. 5,256,797. The method requires warming an anomeric mixture of carbohydrates in a solvent from about 30° C. to about 70° C. to form a supersaturated solution. The solvent may be selected from the group consisting of 1,2-dichloroethane, anisole, glyme, and mixtures thereof. The carbohydrate form a precipitate when the temperature of the solution is lowered and a counter solvent is added. The counter solvent may be selected from the group consisting of methanol, ethanol, toluene, ether, dichloromethane, and mixtures thereof. The resulting carbohydrate crystals are then recovered from the solution and dried.

The nucleobases (R″) employed herein are commonly known to organic chemists and no discussion of their synthesis is necessary. However, in order to be useful in the present glycosylation process, the nucleobase derivatives or their tautomeric equivalents bearing amino or hydroxy groups, preferably contain a protecting group, such as amino protecting groups (W) and/or hydroxy protecting groups (Z), depending on the nature of the nucleobase derivative. The protecting group blocks the hydroxy or amino group which may provide a competing reaction site for the alpha-anomer carbohydrate. The protecting groups are attached to the nucleobase derivative (R′) which is reacted with the beta- or alpha-anomer enriched carbohydrate of formulas II and V and are removed subsequent thereto. A procedure for protecting nucleobase derivatives is described in U.S. Pat. No. 4,526,988.

Preferred amino protecting groups (W) for pyrimidine nucleobase derivatives are selected from the group consisting of silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl; formyl, acetyl, benzoyl and pivalamido; ether forming groups such as methoxymethyl, t-butyl, benzyl, allyl and tetrahydropyranyl; more preferred is trimethylsilyl. Preferred amino protecting groups (W) for purine nucleobase derivatives are selected from the group consisting of alkylcarboxamides, haloalkylcarboxamides and arylcarboxamides such as 2-trialkylsilylethoxymethyl, 4-methoxybenzyl, 3,4-dimethoxybenzyl, t-butyl, phthalamido, tetrahydropyranyl, tetrahydrofuranyl, methoxymethyl ether, methoxythiomethyl, trityl, pivalamido, t-butyldimethylsilyl, t-hexyldimethylsilyl, triisopropylsilyl, trichloroethoxycarbonyl, trifluoroacetyl, naphthoyl, formyl, acetyl; sulfonamides such as alkylsulfonamido and arylsulfonamido, and more preferred is pivalamido. Besides serving as an amino protecting group, the pivalamido protecting group increases the solubility of notoriously insoluble purine nucleobase derivatives and directs the N-glycosidic coupling of the purine bases to the 9 regioisomer as opposed to the 7 regioisomer.

Preferred hydroxy protecting groups (Z) for pyrimidine nucleobase derivatives are selected from silyl ether forming groups such as trialkylsilyl; carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivalamido; preferred is trimethylsilyl. Preferred hydroxy protecting groups (Z) for purine nucleobase derivatives are selected from the group consisting of ether forming groups such as benzyl, t-butyl, trityl, tetrahydropyranyl, tetrahydrofuranyl, methoxymethyl, trityl; esters such as formyl, acetylpropiorl, pivalamido, benzoyl, substituted benzoyl; carbonates such as carbobenzoxy, t-butoxycarbonyl, carbethoxy, vinyloxycarbonyl; carbamates, such as N,N-dialkylcarbamoyl; trialkylsilyl ethers such as t-butyltrimethylsilyl, t-hexyldimethylsilyl, triisopropylsilyl; more preferred is pivalamido.

In providing protecting groups to the nucleobase derivatives of the present process, the protecting group itself may be protected. For example, N-acetylcytosine may be protected with trimethylsilyl to give bis-trimethylsilyl-N-acetylcytosine.

In addition, it is often advisable to convert any keto oxygen atoms on the nucleobase derivatives to enol form. This makes the nucleobase derivative more aromatic and enhances the reactivity of the nucleobase derivative with the alpha-anomer enriched carbohydrate of formulas II and V. It is most convenient to enolize the keto oxygens and provide silyl protecting groups for them. In a preferred embodiment of the present process the nucleobase derivative (R'') is of the formula

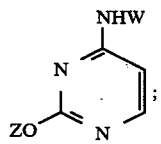

wherein Z and W are trimethylsilyl.

In accordance with the present process, the nucleobase derivative (R'') must be employed in an equimolar amount, relative to the amount of carbohydrate employed. However, it is more preferable to use an excess of nucleobase derivative ranging from about 3 molar equivalents to 30 molar equivalents; more preferably from about 10 molar equivalents to 20 molar equivalents; and most preferably from about 15 molar equivalents to about 20 molar equivalents. In preparing alpha-anomer enriched nucleosides by the present process a smaller amount of nucleobase derivative may be employed in amounts from about 1.5 molar equivalents to about 10 molar equivalents.

Although not critical, it is advisable that the reaction between the beta- and alpha-anomer enriched carbohydrate of formulas II and V and the nucleobase derivative be carried out in a dry atmosphere, e.g. in dry air, nitrogen or argon. This is because certain nucleobase derivatives such as silylated nucleobase derivatives, are moisture sensitive.

The temperature employed in the fusion glycosylation reaction must be sufficient to convert the carbohydrate of formulas II and V and the nucleobase derivative to a molten phase. Therefore, the temperature ranges from about 100° C. to about 160° C. However, a reaction temperature of about 110° C. to about 150° C. is more preferred; while about 130° C. to about 150° C. is most preferred. The glycosylation reaction is preferably carried out under atmospheric conditions and is substantially complete in about 15 minutes to about 2 hours.

The progress of the present fusion glycosylation process may be followed by procedures well known to one of ordinary skill in the art such as high pressure liquid chromatography (HPLC) or thin layer chromatography (TLC) which can be used to detect the presence of nucleoside product.

In accordance with the present fusion glycosylation process, the beta-anomer enriched nucleosides are prepared in an alpha to beta anomer ratio greater than 1:1 to about 9:1.

The final phase of the reaction sequence is the removal of the protecting groups X, Z and/or W from the blocked nucleoside of formula I or IV. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta-anomer enriched nucleosides of formula VI or VII may be extracted and/or isolated from the reaction mixture by the procedure described in U.S. Pat. No. 4,965,374, which is incorporated herein by reference.

The following examples illustrate specific aspects of the present invention and are not intended to limit the scope thereof in any respect and should not be so construed.

Example 1

Preparation of beta-anomer enriched 1-(2'-deoxy-2',2'-difluoro-3',5'-di-O-benzoyl-D-ribofuranosyl)-4-aminopyrimidin-2-one with 3 equivalents of bistrimethylsilylcytosine Bis-trimethylsilylcytosine was prepared by combining 292 mg of cytosine with 2 ml of hexamethyldisilazane, 11 mg of ammonium sulfate and 5 ml of xylenes and refluxing the solution for one hour to form a homogenous solution. The excess xylenes and hexamethyldisilazane were removed leaving behind a molten residue of bis-trimethylsilylcytosine. 400 mg of 2-deoxy-2,2-difluoro-D-ribofuranosyl-3,5-dibenzoyl-1-$\alpha$-methanesulfonate, dissolved in 2 ml of xylenes, were added to the molten bis-trimethylsilylcytosine and the xylenes were removed. The temperature of the reaction mixture was maintained at 160° C. for 15 minutes. HPLC analysis confirmed completion of the reaction. The alpha to beta anomeric ratio of blocked nucleoside product was 1:1.3.

To extract the nucleoside product, the reaction mixture was cooled, diluted in 50 ml of ethyl acetate and washed with 50 ml of 1 N hydrochloric acid.

Example 2

Preparation of beta-anomer enriched 1-(2'-deoxy-2',2'-difluoro-3',5'-di-O-benzoyl-D-ribofuranosyl)-4-ketopyrimidin-2-one with 3 equivalents of bistrimethylsilyluracil Bis-trimethylsilyluracil was prepared by combining 295 mg of uracil with 5 ml of hexamethyldisilazane, 11 mg of ammonium sulfate and 10 ml of 1,2-dichloroethane. The solution was heated to 110° C. for one hour to form a homogenous solution and the excess xylenes and hexamethyldisilazane were removed to form molten bis-trimethylsilyluracil. 200 mg of 2-deoxy-2,2-difluoro-D-ribofuranosyl-3,5-dibenzoyl-1-$\alpha$-methanesulfonate were added to the molten bis-trimethylsilyluracil. The temperature of the reaction mixture was maintained at 150° C. for 2 hours. HPLC analysis confirmed completion of the reaction. The alpha to beta anomeric ratio of blocked nucleoside product was 1:1.8.

To extract the nucleoside product, the reaction mixture was cooled, diluted in 50 ml of ethyl acetate and washed with 50 ml of 1N hydrochloric acid.

Example 3

Preparation of beta-anomer enriched 1-(2'-deoxy-2',2'-difluoro-3',5'-di-O-benzoyl-D-ribofuranosyl)-4-aminopyrimidin-2-one with 10 equivalents of bistrimethylsilylcytosine To 1.12 g of molten bis-trimethylsilylcytosine were added 200 mg of 2-deoxy-2,2-difluoro-D-ribofuranosyl-3,5-dibenzoyl-1-$\alpha$-methanesulfonate. The temperature of the reaction mixture was maintained at 130° C. for 1 hour. HPLC analysis confirmed completion of the reaction. The anomeric ratio of the blocked nucleoside product was 1.7:1 beta to alpha.

To extract the nucleoside product, the reaction mixture was diluted with 100 ml ethyl acetate and washed with 100 ml of 1N hydrochloric acid. A quantitative HPLC analysis of the organic layer indicated that the yield of blocked beta-anomer nucleoside was 50 percent.

Example 4

Preparation of alpha-anomer enriched 1-(2'-deoxy-2',2'-difluoro-3',5'-di-O-benzoyl-D-ribofuranosyl)-4-aminopyrimidin-2-one with 1.5 equivalents of bistrimethylsilylcytosine To 383 mg of bis-trimethylsilylcytosine were added 500 mg in a 50:50 alpha to beta anomeric mixture of 2-deoxy-2,2-difluoro-D-ribofuranosyl-3,5-dibenzoyl-1-methanesulfonate. The temperature of the reaction mixture was maintained at 130° C. for 2 hours. HPLC analysis confirmed completion of the reaction. The beta to alpha anomeric ratio of the blocked nucleoside product was 1:3.

Example 5

Preparation of beta-anomer enriched 1-(2'-deoxy-2',2'-difluoro-3',5'-di-O-benzoyl-D-ribofuranosyl)-4-acetamidopyrimidin-2-one with 3 equivalents of bis-trimethylsilyl-N-acetylcytosine To 500 mg of bis-trimethylsilyl-N-acetylcytosine were added 980 mg of 2-deoxy-2,2-difluoro-D-ribofuranosyl-3,5-dibenzoyl-1-$\alpha$-methanesulfonate. The temperature of the reaction mixture was maintained at 108° C. for 3 hours. HPLC analysis confirmed completion of the reaction. The beta to alpha anomeric ratio of the blocked nucleoside product was 1.4:1.

To extract the nucleoside product, the reaction mixture was cooled, diluted with 25 ml ethyl acetate and washed with 25 ml of 1 N hydrochloric acid. The aqueous layer was washed with 30 ml of ethyl acetate. A quantitative HPLC analysis of the ethyl acetate layer indicated that the yield of blocked beta-anomer nucleoside was 34 percent.

Example 6

Preparation of alpha-anomer enriched 1-(2'-deoxy-2',2'-difluoro-3',5'-di-O-benzoyl-D-ribofuranosyl)-4-aminopyrimidin-2-one with 3 equivalents of bistrimethylsilylcytosine To 332 mg of bis-trimethylsilylcytosine were added 200 mg of 2-deoxy-2,2-difluoro-D-ribofuranosyl-3,5-dibenzoyl-1-D-methanesulfonate. The temperature of the reaction mixture was maintained at 130° C. for 1 hour. HPLC analysis confirmed completion of the reaction. The beta to alpha anomeric ratio of the blocked nucleoside product was 1:6.3.

To extract the nucleoside product, the reaction mixture was cooled, diluted with 20 ml ethyl acetate and washed with 20 ml of 1N hydrochloric acid. The ethyl acetate layer was washed with 20 ml of water. A quantitative HPLC analysis of the ethyl acetate layer indicated that the yield of blocked alpha-anomer nucleoside was 80 percent.

Example 7

Preparation of alpha-anomer enriched 1-(2'-deoxy-2',2'-difluoro-3',5'-di-O-benzoyl-D-ribofuranosyl)-4-aminopyrimidin-2-one with 1.5 equivalents of bistrimethylsilylcytosine To 358 mg of bis-trimethylsilyl-cytosine were added 500 mg of 2-deoxy-2,2-difluoro-D-ribofuranosyl-3,5-dibenzoyl-1-β-toluenesulfonate. The temperature of the reaction mixture was maintained at 140° C. for 30 minutes. HPLC analysis confirmed completion of the reaction. The beta to alpha anomeric ratio of the blocked nucleoside product was 1:4.9.

To extract the nucleoside product, the reaction mixture was cooled, diluted with 50 ml ethyl acetate and washed with 50 ml of 1N hydrochloric acid.

Example 8

Preparation of alpha-anomer enriched 1-(2'-deoxy-2',2'-difluoro-3',5'-di-O-benzoyl-D-ribofuranosyl)-4-aminopyrimidin-2-one with 1.5 equivalents of bistrimethylsilylcytosine To 358 mg of molten bis-trimethylsilylcytosine were added 500 mg of 2-deoxy-2,2-difluoro-D-ribofuranosyl-3,5-dibenzoyl-1-β-toluenesulfonate. The temperature of the reaction mixture was maintained at 130° C. for 2 hours. HPLC analysis confirmed completion of the reaction. The beta to alpha anomeric ratio of the blocked nucleoside product was 1:4.8.

To extract the nucleoside product, the reaction mixture was cooled, diluted with 100 ml ethyl acetate and washed with 100 ml of 1N hydrochloric acid.

Example 9

Preparation of alpha-anomer enriched 1-(2'-deoxy-2',2'-difluoro-3',5'-di-O-benzoyl-D-ribofuranosyl)-4-acetamidopyrimidin-2-one with 3 equivalents of bis-trimethylsilyl-N-acetylcytosine To 500 mg of bis-trimethylsilyl-N-acetylcytosine were added 980 mg of 2-deoxy-2,2-difluoro-D-ribofuranosyl-3,5-dibenzoyl-1-β-methanesulfonate. The temperature of the reaction mixture was maintained at 105°–108° C. for 3 hours. HPLC analysis confirmed completion of the reaction. The beta to alpha anomeric ratio of the blocked nucleoside product was 1:7.

To extract the nucleoside product, the reaction mixture was cooled, diluted with 25 ml ethyl acetate and washed with 25 ml of 1N hydrochloric acid. The two layers were separated and the aqueous layer was washed with 30 ml of ethyl acetate. A quantitative HPLC analysis of the combined ethyl acetate layers indicated that the yield of blocked alpha-anomer nucleoside was 75 percent.

Example 10

Preparation of beta-anomer enriched 1-(2'-deoxy-2',2'-difluoro-3',5'-di-O-benzoyl-D-ribofuranosyl)-4-acetamidopyridin-2-one with 3 equivalents of bis-trimethylsilyl-N-acetylcytosine To 393 mg of molten bis-trimethylsilyl-N-acetylcytosine were added 200 mg of 2-deoxy-2,2-difluoro-D-ribofuranosyl-3,5-dibenzoyl-1-α-methanesulfonate- The temperature of the reaction mixture was maintained at 110° C. for 1 hour. The beta to alpha anomeric ratio of the blocked nucleoside product was 2.3:1.

To extract the nucleoside product, the reaction mixture was diluted with 40 ml ethyl acetate and washed with 25 ml of 1N hydrochloric acid. A quantitative HPLC analysis of the organic layer indicated that the yield of beta-anomer nucleoside was 27 percent.

Example 11

Preparation of beta-anomer enriched 1-(2'-deoxy-2',2'-difluoro-3',5'-di-O-benzoyl-D-ribofuranosyl)-4-aminopyrimidin-2-one with 20 equivalents of bistrimethylsilylcytosine Bis-trimethylsilylcytosine was prepared by combining 4.9 g of cytosine with 90 ml of hexamethyldisilazane, 581 mg of ammonium sulfate and 2 ml of xylenes and heating the solution for two hours to form a homogenous solution. The excess hexamethyldisilazane was removed and a white residue formed. 1 g of 2-deoxy-2,2-difluoro-D-ribofuranosyl-3,5-dibenzoyl-1-α-methanesulfonate, dissolved in 5 ml of acetonitrile, was added to the bis-trimethylsilylcytosine solution and the acetonitrile removed. The temperature of the reaction mixture was maintained at 130° C. under vacuum for 1 hour. HPLC analysis confirmed completion of the reaction. The beta to alpha anomeric ratio of the blocked nucleoside product was 3.9:1.

To extract the nucleoside product, the reaction mixture was diluted with 100 ml dichloromethane and washed sequentially with 100 ml of 1N hydrochloric acid and 200 ml of 5% sodium bicarbonate followed by 200 ml of saturated sodium chloride. The organic layer was dried over magnesium sulfate, filtered and evaporated to 1.03 g of a yellow solid. A quantitative HPLC analysis indicated that the yield of beta-anomer nucleoside was 43 percent.

The following Table shows how the carbohydrate selected, reaction temperature and molar equivalents of nucleobase effect the yield and anomeric ratio of the nucleoside product.

TABLE

| Example | Carbo. | Base (R') | Base (R') Equiv. | Temp. | α/β Nucleoside Ratio | Yield |
|---|---|---|---|---|---|---|
| 7 | β-OTs | Cytosine | 1.5 | 127° C. | 5:1 | N/D |
| 6 | β-OMs | Cytosine | 3.0 | 130° C. | 6:1 | 80% α |
| 9 | β-OMs | N-Acetyl-Cytosine | 3.0 | 127° C. | 7:1 | 75% α |
| 4 | 1:1 α:β-OMs | Cytosine | 1.5 | 130° C. | 3:1 | N/D |
| 1 | α-OMs | Cytosine | 3.0 | 160° C. | 1:1.3 | N/D |
| 3 | α-OMs | Cytosine | 10.0 | 130° C. | 1:1.7 | 50% β |
| 2 | α-OMs | Uracil | 3.0 | 150° C. | 1:1.8 | N/D |
| 5 | α-OMs | N-Acetyl- | 3.0 | 115° C. | 1:1.4 | 34% β |

TABLE-continued

| Example | Carbo. | Base (R') | Base (R') Equiv. | Temp. | α/β Nucleoside Ratio | Yield |
|---|---|---|---|---|---|---|
| 10 | α-OMs | Cytosine N-Acetyl- | 3.0 | 110° C. | 1:2.3 | 27% β |
| 11 | α-OMs | Cytosine | 20.0 | 130° C. | 1:4 | 43% β |

(N/D) means not determined. The carbohydrates (carbo.) are hydroxy protected. α- or β-OMs is alpha- or beta-2,2-difluoro-2-deoxy-D-ribofuranosyl-3,5-dibenzoyl-1-methanesulfonate and β- or α-OTs is beta- or alpha- 2,2-difluoro-2-deoxy-D-ribofuranosyl-3,5-dibenzoyl-1-toluenesulfonate. The yields are based on the total amount of carbohydrate and were calculated from a quantitative reverse phase HPLC analysis, wherein the corresponding solution product peak was compared with a standard, 1-(2'-deoxy-2',2'-difluoro-3',5'-di-O-benzoyl-beta-D-ribofuranosyl)-4-aminopyrimidin-2-one. The nucleoside base protecting group in each example is trimethylsilyl.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective fusion glycosylation process for preparing a beta-anomer enriched nucleoside of the formula

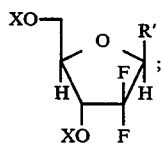
(IB)

wherein each X is independently selected from hydroxy protecting groups and R' is a nucleobase selected from the group consisting of

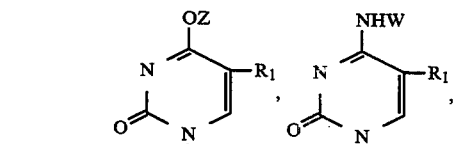

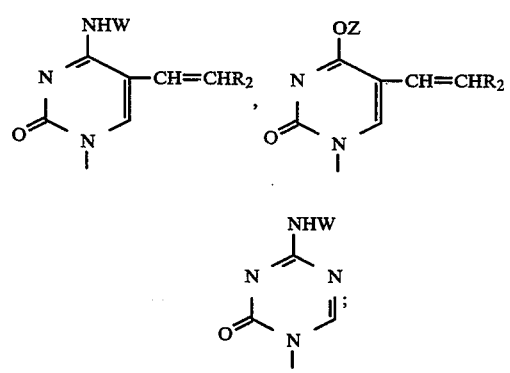

wherein R₁ is selected from the group consisting of hydrogen C₁-C₇alkyl and halo; R₂ is selected from the group consisting of hydrogen, C₁-C₇alkyl and halo; Z is a hydroxy protecting group and W is an amino protecting group; comprising reacting alpha-anomer 2,2-difluorocarbohydrate in a anomer ratio of greater than 1:1 alpha to beta of the formula

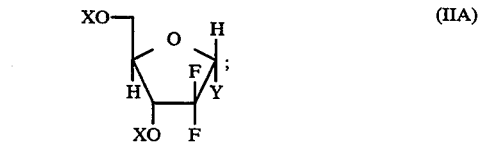
(IIA)

wherein Y is selected from the group consisting of C₁-C₇alkylsulfonyloxy, arylsulfonyloxy, substituted C₁-C₇alkylsulfonyloxy and substituted arylsulfonyloxy and X is as defined above; with at least 3 molar equivalents; of a nucleobase derivative R" selected from the group consisting of

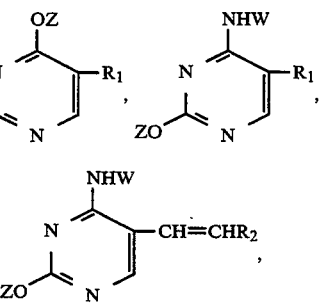

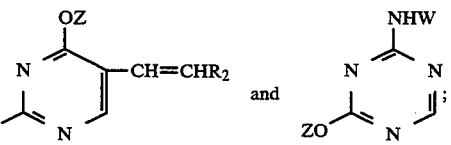

wherein R₁, R₂, Z and W are as defined above; at a temperature ranging from about 100° C. to about 160° C. in the absence of a catalyst and a solvent.

2. The process of claim 1 wherein the amount of R" is greater than 3 molar equivalents to about 30 molar equivalents.

3. The process of claim 1 wherein Y is selected from the group consisting of methanesulfonyloxy, 2-chloroethanesulfonyloxy, toluenesulfonyloxy, p-nitrobenzenesulfonyloxy and p-bromobenzenesulfonyloxy.

4. The process of claim 1 wherein X is selected from the group consisting of benzoyl; benzoyl substituted by a group selected from the group consisting of cyano, halo, carbo C₁-C₇alkoxy, toluoyl, nitro, C₁-C₇alkoxy, C₁-C₇alkyl and diC₁-C₇alkylamino; and benzoyl disubstituted by groups independently selected from the group consisting of cyano, halo, carbo C₁-C₇alkoxy, soluoyl, nitro, C₁-C₇alkyl and diC₁-C₇alkylamino.

5. The process of claim 1 wherein Z and W are selected from the group consisting of triC₁-C₇alkylsilyl, t-butoxycarbonyl, benzyloxycarbonyl, 4-methoxybenzyloxycarbonyl, 4-nitrobenzyloxycarbonyl, formyl and acetyl.

6. The process of claim 5 wherein Z and W are trimethylsilyl.

7. The process of claim 1 wherein R" is of the formula

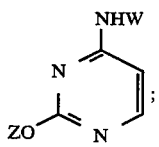

wherein Z and W are trimethylsilyl.

8. The process of claim 7 wherein Y is methanesulfonyloxy.

9. The process of claim 7 wherein X is benzoyl.

10. A stereoselective glycosylation process for preparing a beta-anomer enriched nucleoside of the formula

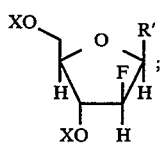

wherein each X is independently selected from hydroxy protecting groups and R' is a nucleobase selected from the group consisting of

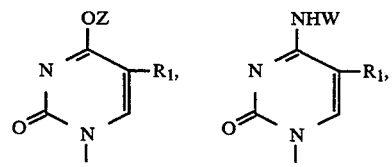

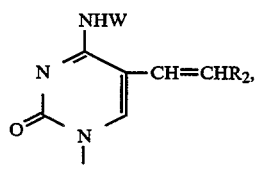

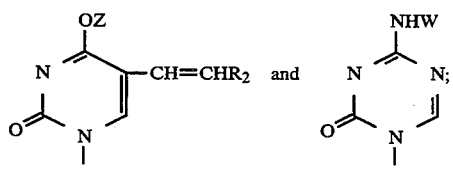

wherein $R_1$ is selected from the group consisting of hydrogen, $C_1$-$C_7$alkyl and halo; $R_2$ is selected from the group consisting of hydrogen, $C_1$-$C_7$alkyl and halo; Z is a hydroxy protecting group and W is an amine protecting group; comprising reacting alpha-anomer 2-fluorocarbohydrate in a anomer ratio of greater than 1:1 alpha to beta of the formula

wherein Y i8 selected from the group consisting of $C_1$-$C_7$alkylsulfonyloxy, arylsulfonyloxy, substituted $C_1$-$C_7$alkylsulfonyloxy and substituted arylsulfonyloxy and X is as defined above; with at least 3 molar equivalents of a nucleobase derivative, R" selected from the group consisting of

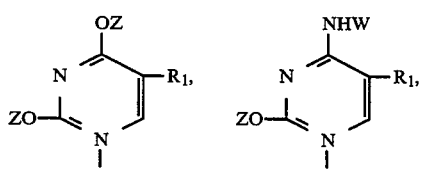

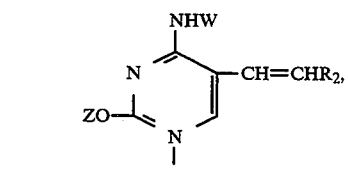

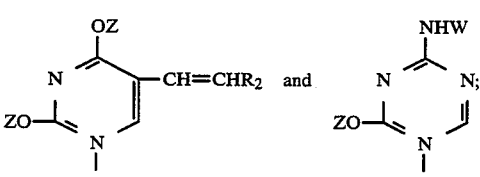

wherein $R_1$, $R_2$, Z and W are as defined above; at a temperature ranging from about 100° C. to about 160° C. in the absence of a catalyst and a solvent.

11. The process of claim 10 wherein the amount of R" is greater than 3 molar equivalents to about 30 molar equivalents.

12. The process of claim 10 wherein Y is selected from the group consisting of methanesulfonyloxy, 2-chloroethanesulfonyloxy, toluenesulfonyloxy, p-nitrobenzenesulfonyloxy and p-bromobenzenesulfonyloxy.

13. The process of claim 10 wherein X is selected from the group consisting of benzoyl; benzoyl substituted by a group selected from the group consisting of cyano, halo, carbo $C_1$-$C_7$alkoxy, toluoyl, nitro, $C_1$-$C_7$alkoxy, $C_1$-$C_7$alkyl and di$C_1$-$C_7$alkylamino; and benzoyl di-substituted by groups independently selected from the group consisting of cyano, halo, carbo $C_1$-$C_7$alkoxy, toluoyl, nitro, $C_1$-$C_7$alkoxy, $C_1$-$C_7$alkyl and di$C_1$-$C_7$alkylamino.

14. The process of claim 10 wherein Z and W are selected from the group consisting of tri$C_1$-$C_7$alkylsilyl, t-butoxycarbonyl, benzyloxycarbonyl, 4-methoxybenzyloxycarbonyl, 4-nitrobenzyloxycarbonyl, formyl and acetyl.

15. The process of claim 14 wherein Z and W are trimethylsilyl.

16. The process of claim 1 further comprising deblocking to form a beta-anomer enriched nucleoside of the formula

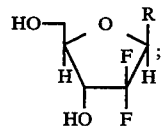 (VIB)

wherein R is a deblocked nucleobase selected from the group consisting of

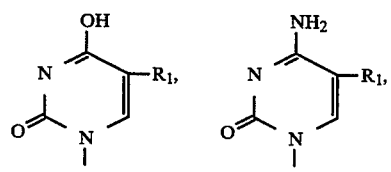

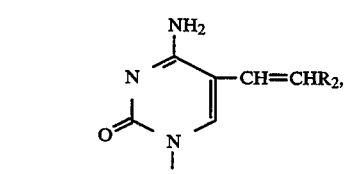

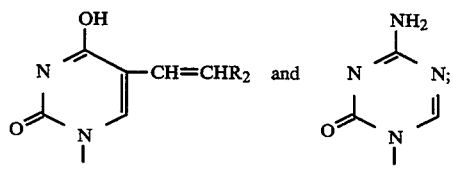

wherein $R_1$ is selected from the group consisting of hydrogen, $C_1$–$C_7$alkyl and halo; $R_2$ is selected from the group consisting of hydrogen, $C_1$–$C_7$alkyl and halo.

17. The process of claim 16 wherein R is of the formula

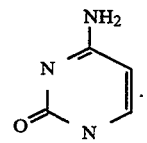

18. The process of claim 10 further comprising deblocking to form a beta-anomer enriched nucleoside of the formula

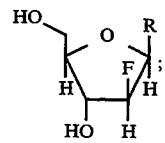 (VIIB)

wherein R is a deblocked nucleobase selected from the group consisting of

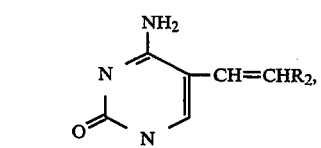

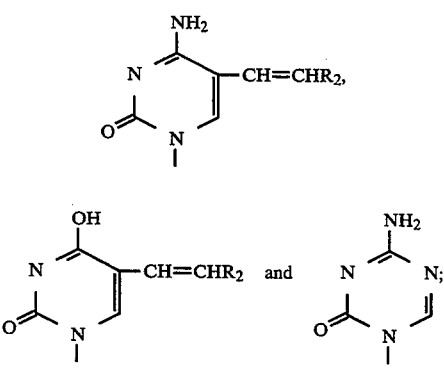

wherein $R_1$ is selected from the group consisting of hydrogen, $C_7$alkyl and halo; $R_2$ is selected from the group consisting of hydrogen, $C_1$–$C_7$alkyl and halo.

* * * * *

UNITED STATES PATENT AND TRADEMARK OFFICE
CERTIFICATE OF CORRECTION

PATENT NO. : 5,401,838

DATED : March 28, 1995

INVENTOR : Ta-Sen Chou

It is certified that an error appears in the above-identified patent and that said Letters Patent is hereby corrected as shown below:

Column 19, line 21, "stereoselective glycosylation" should read, -- stereoselective fusion glycosylation --.

Column 19, line 64, "amine" should read, -- amino --.

Column 22, line 46, "$C_7$ alkyl" should read, -- $C_1$-$C_7$ alkyl --.

Signed and Sealed this

Fifth Day of September, 1995

Attest:

BRUCE LEHMAN

Attesting Officer

Commissioner of Patents and Trademarks